United States Patent
Dubois et al.

(10) Patent No.: US 7,916,307 B2
(45) Date of Patent: Mar. 29, 2011

(54) PRE-AMPLIFIER FOR DETECTION LASERS WITHIN LASER ULTRASONIC INSPECTION SYSTEMS

(75) Inventors: Marc Dubois, Keller, TX (US); Thomas E. Drake, Jr., Fort Worth, TX (US); Kenneth R. Yawn, Weatherford, TX (US)

(73) Assignee: Lockheed Martin Corporation, Bethesda, MD (US)

( * ) Notice: Subject to any disclaimer, the term of this patent is extended or adjusted under 35 U.S.C. 154(b) by 0 days.

(21) Appl. No.: 11/688,379

(22) Filed: Mar. 20, 2007

(65) Prior Publication Data
US 2008/0181268 A1    Jul. 31, 2008

Related U.S. Application Data

(60) Provisional application No. 60/871,680, filed on Dec. 22, 2006.

(51) Int. Cl.
*H01S 3/13*     (2006.01)
*G01B 11/02*    (2006.01)
*H01P 7/00*     (2006.01)

(52) U.S. Cl. ............. 356/502; 372/25; 372/30; 73/596

(58) Field of Classification Search ............... 372/30; 356/502
See application file for complete search history.

(56) References Cited

U.S. PATENT DOCUMENTS

| 6,081,369 | A   | * | 6/2000  | Waarts et al. ........... 359/341.33 |
| 6,657,733 | B1  | * | 12/2003 | Drake, Jr. ..................... 356/511 |
| 6,885,683 | B1  | * | 4/2005  | Fermann et al. ................ 372/25 |
| 7,342,228 | B1  | * | 3/2008  | O'Connell et al. ...... 250/339.06 |
| 2005/0099634 | A1 | * | 5/2005 | Dubois et al. ................ 356/502 |
| 2008/0219299 | A1 | * | 9/2008 | Lewis ............................... 372/6 |

FOREIGN PATENT DOCUMENTS

| EP | 1220380 A2 | 3/2002 |
| EP | 1530032 A2 | 5/2005 |
| WO | 01/27606 A1 | 4/2001 |
| WO | 03/100363 A2 | 12/2003 |

* cited by examiner

*Primary Examiner* — Minsun Harvey
*Assistant Examiner* — Phillip Nguyen
(74) *Attorney, Agent, or Firm* — Bracewell & Giuliani LLP

(57) ABSTRACT

A pulse detection laser is provided. The pulse detection laser includes a single frequency oscillator, a continuous pre-amplifier, and a pulsed amplifier. The single frequency oscillator generates a seed laser beam and is optically coupled to the continuous preamplifier. The continuous pre-amplifier amplifies the seed laser to produce an intermediate power laser beam. A pulsed amplifier optically coupled to the continuous pre-amplifier receives the intermediate power laser beam and amplifies the intermediate power laser beam to produce a pulse detection laser beam. One task of this pulse detection laser is to illuminate ultrasonic displacements. Light from the laser is scattered, collected, and analyzed with an interferometer to demodulate the ultrasonic displacements caused by the return echoes of the ultrasound at the surface of the part.

18 Claims, 6 Drawing Sheets

PRE-AMPLIFIER FOR DETECTION LASERS WITHIN LASER ULTRASONIC INSPECTION SYSTEMS

RELATED APPLICATIONS

This application claims priority to and incorporates by reference in its entirety for all purposes U.S. Provisional Application No. 60/871,680 filed on 22 Dec. 2006 entitled "ARTICULATED ROBOT FOR LASER ULTRASONIC INSPECTION" to Thomas E. Drake.

This application incorporates by reference in its entirety for all purposes U.S. Provisional Application No. 60/091,240 filed on 30 Jun. 1998.

This application incorporates by reference in its entirety for all purposes U.S. Provisional Application No. 60/091,229 filed on 30 Jun. 1998 entitled "METHOD AND APPARATUS FOR DETECTING ULTRASONIC SURFACE DISPLACEMENTS USING POST-COLLECTION OPTICAL AMPLIFICATION" to Thomas E. Drake.

This application incorporates by reference in its entirety for all purposes U.S. patent application Ser. No. 10/753,208 filed on 7 Jan. 2004 and entitled "REMOTE LASER BEAM DELIVERY SYSTEM AND METHOD FOR USE WITH A ROBOTIC POSITIONING SYSTEM FOR ULTRASONIC TESTING PURPOSES" to Thomas E. Drake.

This application incorporates by reference in its entirety U.S. patent application Ser. No. 10/634,342 filed on 12 Feb. 2004 and entitled "METHOD AND APPARATUS FOR ULTRASONIC LASER TESTING" to Thomas E. Drake.

TECHNICAL FIELD OF THE INVENTION

The present invention relates generally to an apparatus and method of non-destructive evaluation of materials, and more particularly, to a detection laser within an ultrasonic laser inspection system used to perform non-destructive evaluations of materials.

BACKGROUND OF THE INVENTION

In recent years, the use of advanced composite structures has experienced tremendous growth in the aerospace, automotive, and many other commercial industries. While composite materials offer significant improvements in performance, they require strict quality control procedures in both the manufacturing processes and after the materials are in service in finished products. Specifically, non-destructive evaluation (NDE) methods must assess the structural integrity of composite materials. This assessment detects inclusions, delaminations and porosities. Conventional NDE methods are slow, labor-intensive, and costly. As a result, testing procedures adversely increase the manufacturing costs associated with composite structures.

Various methods and apparatuses have been proposed to assess the structural integrity of composite structures. One solution uses an ultrasonic source to generate ultrasonic surface displacements in a work piece which are then measured and analyzed. Often, the external source of ultrasound is a pulsed generation laser beam directed at the target. Laser light from a separate detection laser is scattered by the surface the work piece. The detection laser light is phase modulated by the ultrasonic displacements. Notice that a modulation of phase as a function of time corresponds also to a frequency modulation and either type of modulation can be used to describe the process depicted here. Collection optics then collect the scattered laser energy. The collection optics are coupled to an interferometer or other device. The interferometer demodulates the ultrasonic displacement informant and data about the structural integrity of the composite structure can be obtained through analysis of the resulting signal. Laser ultrasound has been shown to be very effective for the inspection of parts during the manufacturing process.

However, the equipment used for laser ultrasound is custom-designed and is presently a limiting factors regarding inspection speed. Previous solid-state detection lasers used either flash-lamp pumped rod architectures or diode-pumped slab configurations to amplify a low power master oscillator laser. These configurations are generically referred to as master oscillator power amplifier (MOPA) lasers.

Inspection speed is currently limited by the pulse rate of the lasers. Flash-lamp pumped lasers can only operate at 100 Hz and the lamps typically only last 10's of millions of shots. Therefore these lasers are slow and expensive to operate. Diode-pumped slabs are much faster (400 Hz is current limit and 1 Khz may be possible) but they use very expensive custom-manufactured diode arrays to pulse-pump the slabs and create a great amount of heat which can induce thermal distortion. Although diode array lifetimes are getting better, some have lasted 102 shots, they have historically been a concern due to both high-cost, reliability and thermal distortion. High-power pulsed-diode pumping of a crystal slab will introduce thermal distortions into the slab that ultimately limits the waveform quality of the laser beam. Wavefront distortion can limit the useful power of a laser and prevent efficient fiber optic delivery of the beam to the target. Each diode bar in the array may have a peak power of 40 W to 100 W and they must be physically close to each other in order to efficiently pump the side of the laser slab. The total number of diode bars in an array may be 50-100 (an array will pump each side of the slab, so possibly 200 diode bars may be used). Heat removal is a significant design issue for both the diode arrays and the slab.

SUMMARY OF THE INVENTION

Embodiments of the present invention are directed to systems and methods that substantially address the above identified needs and other needs as well. The embodiments of the present invention are further described in the following description and claims. Advantages and features of embodiments of the present invention may become apparent from the description, accompanying drawings and claims.

Embodiments of the present invention relate to an improved laser for the optical detection of ultrasound. A pulse detection laser is provided by embodiments of the present invention. The pulse detection laser includes a single frequency oscillator, a continuous pre-amplifier, and a pulsed amplifier. The single frequency oscillator generates a seed laser beam and is optically coupled to the continuous preamplifier. The continuous pre-amplifier amplifies the seed laser to produce an intermediate power laser beam. A pulsed amplifier optically coupled to the continuous pre-amplifier receives the intermediate power laser beam and amplifies the intermediate power laser beam to produce a pulse detection laser beam. One task of this pulse detection laser is to illuminate ultrasonic displacements. Light from the laser is scattered, collected, and analyzed with an interferometer to demodulate the ultrasonic displacements caused by the return echoes of the ultrasound at the surface of the part.

In another embodiment, a method for generating the detection laser beam is provided. This method involves generating a seed laser beam with a master oscillator. The seed laser beam can then be amplified with a continuous preamplifier and a diode pumped pulse laser amplifier to produce a pulsed detection laser beam.

Another embodiment provides an ultrasonic surface inspection system operable to detect ultrasonic surface displacements on a remote target. This system includes an ultrasound generation system, a detection laser such as the one described above, collection optics, and a processor. The ultrasound generation system produces ultrasonic surface displacements at the remote target. This may be done mechanically or using a laser ultrasound generation system. The diode pumped detection laser generates a detection laser beam that substantially illuminates the ultrasonic surface displacements at the remote target. Collection optics collect phase modulated light from the diode pumped detection fiber laser either reflected or scattered by the remote target. The processor may optically process the phase modulated light to produce an output signal containing data representative of the ultrasonic surface displacements at the remote target. Then the processor may process the output signal to assess the structural integrity of the remote target.

In yet another embodiment the present invention provides a large area composite inspection system to measure ultrasonic surface displacements on the surface of a remote target in order to assess the structural integrity of the remote target. This large area composite inspection system may include an ultrasound generation system, a pulsed detection laser, collection optics, an optical processor, and a signal processor. The ultrasound generation system produces ultrasonic displacements at the remote target. A detection laser then illuminates the ultrasonic surface displacements with a detection laser beam. A scanning assembly generates relative motion between the illumination spot of the detection laser and the remote target. This may be achieved by any combination of scanning the detection laser beam by redirecting the beam, moving the detection laser beam, or moving the remote target. The collection optics collect phase modulated light from the detection laser beam reflected or scattered by the ultrasonic surface displacements at the remote target. The optical processor then processes the phase modulated light collected by the collection optics to produce an output signal. The signal processor then processes the output signal of the optical processor to obtain data representative of the ultrasonic surface displacements. This data may then be used to assess the integrity of the remote target. For example the internal structure of a composite material.

BRIEF DESCRIPTION OF THE DRAWINGS

For a more complete understanding of the present invention and the advantages thereof, reference is now made to the following description taken in conjunction with the accompanying drawings in which like reference numerals indicate like features and wherein.

DETAILED DESCRIPTION OF THE INVENTION

Figure 1:
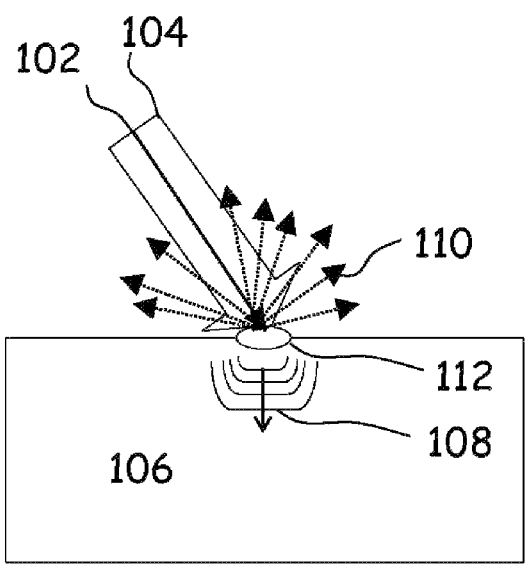
FIG. 1 illustrates the use of generation laser beam and a detection laser beam to generate and detect laser ultrasonic displacements in accordance with an embodiment of the present invention.

Preferred embodiments of the present invention are illustrated in the FIGs., like numerals being used to refer to like and corresponding parts of the various drawings.

Embodiments of the present invention provide a detection laser for use within a laser ultrasound system. A pulse detection laser is provided by embodiments of the present invention. The pulse detection laser includes a single frequency oscillator, a continuous pre-amplifier, and a pulsed amplifier. The single frequency oscillator generates a seed laser beam and is optically coupled to the continuous preamplifier. The continuous pre-amplifier amplifies the seed laser to produce an intermediate power laser beam. A pulsed amplifier optically coupled to the continuous pre-amplifier receives the intermediate power laser beam and amplifies the intermediate power laser beam to produce a pulse detection laser beam. One task of this pulse detection laser is to illuminate ultrasonic displacements. Light from the laser is scattered, collected, and analyzed with an interferometer to demodulate the ultrasonic displacements caused by the return echoes of the ultrasound at the surface of the part.

This pulse detection laser can be constructed in many ways. One approach is to use single-frequency non-planar ring oscillator (NPRO) as a master oscillator and then subsequent amplification by two or more laser amplifiers.

Previous solid-state detection lasers used either flash-lamp pumped rod architectures or diode-pumped slab configurations to amplify a low power master oscillator laser. These configurations are generically referred to as master oscillator power amplifier (MOPA) lasers. Flash-lamp pumped laser can operate at approximately 100 Hz and diode-pumped slab designs operate easily at 400 Hz, but could be extended to 1 kHz. A typical pulse profile would be to reach a peak power of 1000 W for of 50 us-100 us. The pulse rate of the laser is one of the factors that limit the inspection throughput of the LaserUT system.

Interferometric detection of ultrasonic displacements requires a stable frequency detection laser beam. The required frequency stability can be achieved with relatively low power laser (i.e. a few mW to 1 W). However, laser-ultrasonic inspection typically requires around 500 to 1000 Watts peak powers. Those peak powers are achieved by amplifying the low power single-frequency lasers. High peak powers are achieved by using pulsed amplifiers that produce the required peak powers for short durations (i.e. microseconds (.mu.s)). Amplification of the low power single-frequency laser to produce the pulsed detection laser requires significant laser gain and several passes through the amplifier medium. High laser gain and repeated passes through the amplifier medium can distort the laser beam. The level of pulsed pumping power and the number of passes in the amplifying medium is reduced within embodiments of the present invention by applying a continuous pre-amplifier to amplify the stable low power single-frequency laser to an intermediate power level laser beam. This intermediate power level laser beam may be on the order of 5 to 10 Watts.

Embodiments of the present invention provide for faster inspection rates, improved system reliability, lower operation costs and enable mobile and portable systems. Inspection speed is currently limited by the pulse rate of the lasers. Flash-lamp pumped lasers can only operate at 100 Hz and the lamps typically only last 10's of millions of shots. Therefore these lasers are slow and expensive to operate. Diode-pumped slabs are much faster (400 Hz is current limit and 1 KHz may be possible) but they use very expensive custom-manufactured diode arrays to pulse-pump the slabs. Although diode array lifetimes have improved, some have lasted $10^2$ shots, they have historically been a concern due to both high-cost and reliability. The use of continuous diodes within the pre-amplifier reduces the number of pump diodes required within the amplifier. Thus, the distortions, such as the thermal distortions introduced by the high-power pulsed-diode pumping of a crystal slab, that ultimately limit the waveform quality of the laser beam may be reduced. Wavefront distortion can limit the useful power of a laser and prevent efficient fiber optic delivery of the beam to the target.

Each diode bar in the diode array may have a peak power of 40 W to 100 W and they must be physically close to each other in order to efficiently pump the side of the laser slab. The total number of diode bars in an array may be 50-100 (an array will pump each side of the slab, so possibly 200 diode bars may be used). Heat removal and thermal distortion becomes a significant design issue for both the diode arrays and the slab.

The use of small continuous wave (cw) diodes to amplify the seed laser within the pre-amplifier has several advantages. First, the use of continuous diodes allows the number of pump diodes to be reduced. Continuous diodes are less expensive and more reliable. Additionally, Because the gain requirement associated with the pump diodes is less, the final laser beam after amplification has improved propagation properties. Heat removal requirements from the pumped diodes within the amplifier are also reduced.

When the laser stages (i.e. single frequency oscillator, a continuous pre-amplifier, and a pulsed amplifier) are implemented at least partially as a fiber laser, thermal management of a fiber laser/amplifier is more easily handled than within a traditional bulk crystal gain medium. The ratio of the fiber surface area (where heat is extracted) to the volume is many orders-of-magnitude larger than the surface-to-volume ratio for a slab amplifier. The fiber-laser can be operated in a single-mode (TEM00) with very little wavefront distortion ($M^2<1.2$). With a fiber laser which can now operate either in a cw mode or in a modulated (pulsed) mode, the speed limitation is not the laser speed but becomes the ultrasound propagation time and scanning capabilities. Effective scan rates could be 10 kHz or higher.

FIG. 1 depicts the use of a detection laser in accordance with embodiments of the present invention. Two incoming laser beams that generate and detect laser ultrasonic displacements are directed to the surface of an object. Laser beam 102 generates ultrasound while detection Laser beam 104 detects the ultrasound at a remote target 106, such as, but not limited to, a composite material under test. As shown, these lasers may be coaxially applied to remote target 106. Generation laser beam 102 causes thermo-elastic expansion 112 in target 106 that results in the formation of ultrasonic waves 108. In a different embodiment, generation laser beam causes ablation in target 106. Ultrasonic waves 108 propagate in target 106 and modulate detection laser beam 104 to produce phase-modulated light 110 that is scattered and/or reflected by surface of target 106. The scattered light is collected and processed to obtain information of the internal structure of remote target 106. It is to be understood that when phase modulation is mentioned here, it corresponds also to a frequency modulation. The reason is that the time derivative of a phase modulation corresponds to the frequency modulation. Since the term modulation in the present context means variation as a function of time, any phase modulation corresponds also to a frequency modulation.

Figure 2:
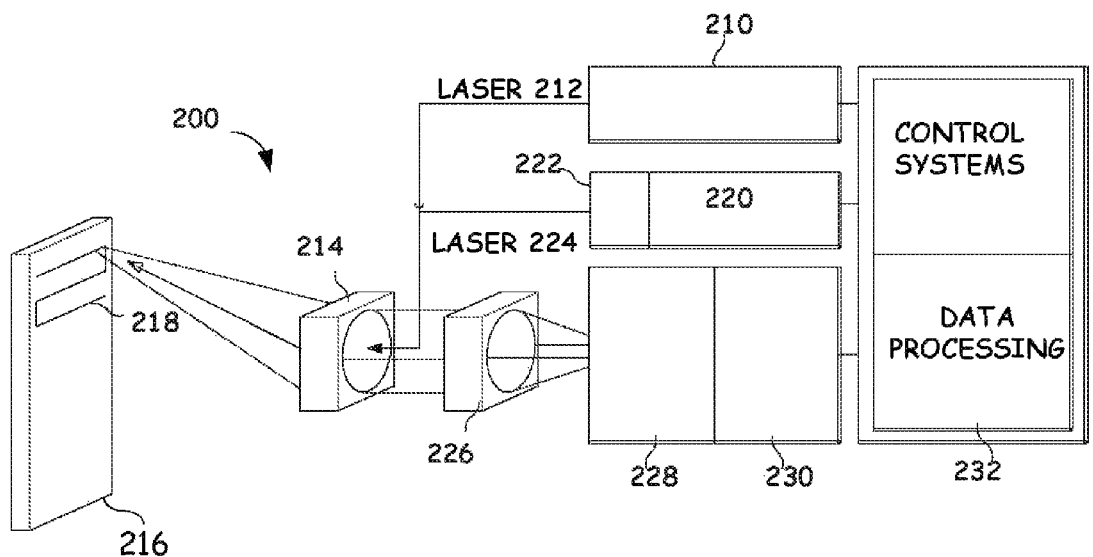
FIG. 2 provides a block diagram to show the basic components of laser ultrasound system.

FIG. 2 provides a block diagram with the basic components for performing ultrasonic laser testing. Generation laser 210 produces laser beam 212 which optical assembly 214 directs to target 216. As shown, optical assembly 214 includes a scanner or other like mechanism that moves laser beams 212 and 224 along a scan or test plan 218. Scan or test plan 218 can also be created by the movement of target 216 or by a combination of movement of target 216 and movement of laser beams 212 and 224 through assembly 214. Optical assembly 214 may include visual cameras, depth cameras, range detectors, narrow and cameras or other like optical sensors known to those having skill in the art. These optical sensors each may require calibrations prior to performing an inspection. This calibration verifies the ability of the system to integrate information gathered by various sensors. Generation laser 210 produces an ultrasonic wave 108 within target 216.

The ultrasonic wave 108 is the result of thermo-elastic expansion 112 of the composite material as the material absorbs the generation laser beam. Remote target 216 such as, but not limited to, a composite material readily absorbs generation laser beam 212 without ablating or breaking down. Higher powered generation lasers are not necessarily preferred to overcome SNR issues as these can result in ablation. In other embodiments, depending on the material being tested, some ablation may be acceptable in order to increase the SNR of the detected signal. Generation laser beam 212 has appropriate pulse duration to induce ultrasonic surface deformations. For example, a transverse-excited atmospheric (TEA) $CO_2$ laser can produce a 10.6 micron wavelength beam for a 100 nanosecond pulse. The power of the laser must be sufficient to deliver, for example, a 0.25 joule pulse to the target, which may require a 100 watt laser operating at a 400 Hz pulse repetition rate. Generation laser beam 212 is absorbed and creates heat into the target surface thereby causing thermo-elastic expansion without significant ablation in one embodiment of the present invention. In a different embodiment of the present invention, generation laser beam 212 is absorbed and creates enough heat in the target surface to cause ablation that becomes the main mechanism of ultrasonic wave generation.

Illumination or detection laser 220 operating in pulsed mode or continuous wave mode does not induce ultrasonic displacements. For example, an Nd:YAG laser can be used. The power of this laser must be sufficient to deliver, for example, a 100 milli-joule, 100 micro-second pulse, which may require a one kilo-watt laser. Detection Laser 220 generates detection laser beam 222. Detection laser 220 may be a pulse detection laser as provided by embodiments of the present invention. Various embodiments of this pulse detection laser will be discussed with reference to FIG. 3 and following. Detection Laser 220 includes or optically couples to filtering mechanism 224 to remove noise from detection laser beam 224. Optical assembly 214 directs Detection Laser beam 224 to the surface of composite material 216 which scatters and/or reflects detection laser beam 224. Resultant phase modulated light is collected by collection optics 226. As shown here, scattered and/or reflected detection laser light travels back through optical assembly 214. Optional optical processor 228 and interferometer 230 process the phase modulated light to produce a signal containing information representative of the ultrasonic displacements at the surface of composite material 216. Data processing and control system 232 coordinate operation of the laser ultrasound system components.

Data processing and control system 232 may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions stored in memory. The memory may be a single memory device or a plurality of memory devices. Such a memory device may be a read-only memory, random access memory, volatile memory, non-volatile memory, static memory, dynamic memory, flash memory, cache memory, and/or any device that stores digital information. The memory stores, and data processing and control system 232 executes, operational instructions corresponding to at least some of the steps and/or functions as will be illustrated.

Figure 3:
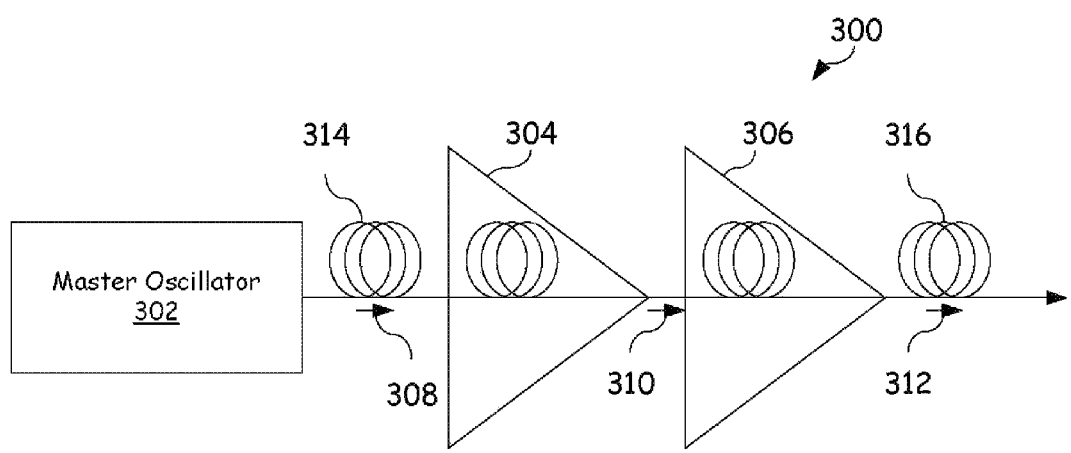
FIG. 3 depicts a pulse detection laser that uses a continuous pre-amplifier to produce a pulsed detection laser beam in accordance with embodiments of the present invention.

FIG. 3 depicts a pulse detection laser 300 which may be used as detection laser 220 of FIG. 2 in accordance with embodiments of the present invention. Pulse detection laser 300 includes a single frequency oscillator 302, a continuous pre-amplifier 304, and a pulsed amplifier 306. Single frequency oscillator 302 generates a seed laser beam 308 and is optically coupled to the continuous preamplifier 304. For illustrative purposes the power of seed laser beam 308 may be approximately 2 mW to 1 W. Continuous pre-amplifier 304 amplifies seed laser beam 308 to produce an intermediate power laser beam 310. In this embodiment and in the following embodiments, continuous pre-amplifier 304 might be composed of a single amplification stage or more than one amplification stage. Pulsed amplifier 306 optically couples to continuous pre-amplifier 304, receives intermediate power laser beam 310, and amplifies the intermediate power laser beam 310 to produce a pulse detection laser beam 312. In this embodiment and in the following embodiments, the pulsed amplifier 306 can be a continuous amplifier that has its output modulated to accommodate the acquisition rate of the laser-ultrasonic system and hence limit the total detection laser power absorbed by the target. In some cases, the output power of the continuous pre-amplifier 304, or part of it, can be varied. This power variation can be necessary to protect the detection electronics when the target strongly reflects the detection laser beam. These cases are very limited and therefore the pre-amplifier 304 is considered as continuous (CW). For illustrative purposes the power of seed laser beam 308 may be approximately 2 mW to 1 W; the power of intermediate power laser beam 310 may be approximately 10-100 W cw; and the power of pulse detection laser beam 312 may be approximately 500-1000 W pulsed.

The embodiment of the detection laser 300 depicted in FIG. 3 may use a master oscillator 302 that may be fiber coupled to a diode pumped fiber continuous pre-amplifier 306 that operates continuously with optical fibers 314. Similarly, the amplified laser beam 310 produced by pre-amplifier 306 may be delivered to pulsed amplifier 306 via optical fiber as well. pulse detection laser beam 312 is applied to the materials to be inspected with optical fiber 316. Master oscillator 302 may be a diode pumped non-planar ring oscillator (NPRO) having a fiber-coupled output that allows the generated seed detection laser beam 308 to be provided via an optical fiber 314 to pre-amplifier 304. Another approach may construct an all fiber single-frequency laser using a fiber laser as the master oscillator 302 and one or more fiber lasers such as diode pumped fiber amplifier as pre-amplifier 304 and amplifier 306 as well.

In this embodiment, pre-amplifier 304 may be a diode pumped fiber continuous pre-amplifier having a fiber-coupled output that allows the intermediate power laser beam 310 to be provided via an optical fiber to amplifier 306. The pre-amplifier can also be a diode or lamp pumped rod or slab. For illustrative purposes, the lasing material may be Nd:YAG, Yb:YAG, Nd:YVO4 to name a few. This material may be configured as a single-pass or multi-pass amplifier. Amplifier 306 may be a diode pumped fiber pulsed amplifier having a fiber-coupled output that allows the pulse detection laser beam via an optical fiber.

Figure 4:
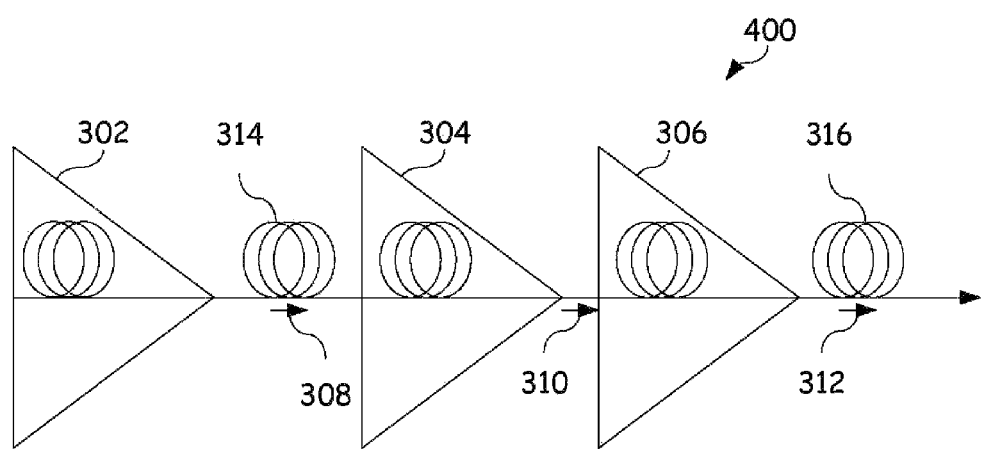
FIG. 4 depicts a fiber pulse detection laser that uses a continuous fiber laser pre-amplifier to produce a pulsed detection laser beam in accordance with embodiments of the present invention.

FIG. 4 depicts a second embodiment of detection laser 400 that uses fiber lasers exclusively in accordance with an embodiment of the present invention. In this case, master oscillator 302 is coupled to two or more diode pumped fiber amplifiers 304 and 306. As before, master oscillator 302 has a fiber coupled output to optical fiber 314. Master oscillator 302 may be a diode pumped single frequency fiber laser having a fiber-coupled output. Master oscillator 302 generates seed laser 308 which is delivered to diode pumped pre-amplifier 304 via optical fiber 314. For purposes of example, the laser beam 302 produced by master oscillator 302, may be a 2-25 mW laser. Diode pumped continuous pre-amplifier 304 may increase the power of intermediate power laser beam 310 to 10-100 W. Amplifier 306 may be used to further increase the power of the detection laser to 500-1000 W pulsed. The output of the fiber pumped amplifier 306 is then delivered to the materials to be tested using optical fiber 316.

Figure 5:
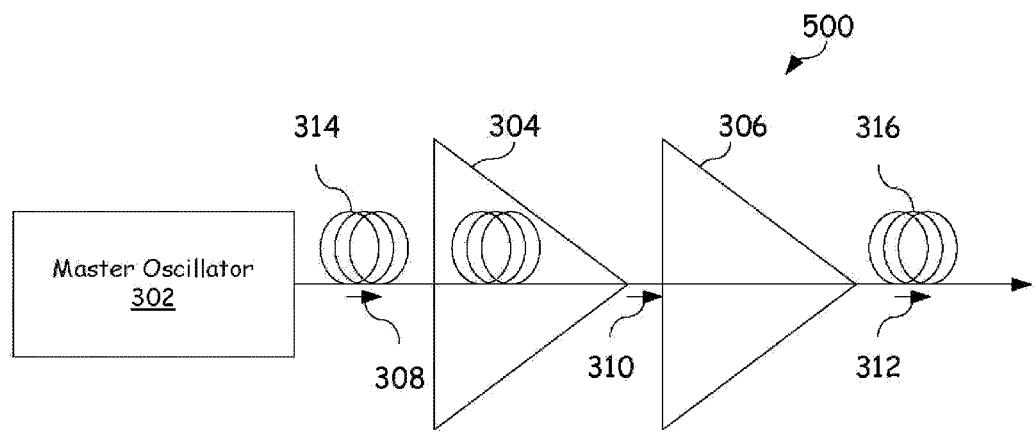
FIG. 5 depicts a pulse detection laser that uses a continuous pre-amplifier to produce a pulsed detection laser beam in accordance with embodiments of the present invention.

FIG. 5 depicts a pulse detection laser 500 which may be used as detection laser in accordance with embodiments of the present invention. Pulse detection laser 500 includes a single frequency oscillator 302, a continuous pre-amplifier 304, and a pulsed amplifier 306. This embodiment operates similarly to that described with reference to FIG. 3. In this embodiment, amplifier 306 of FIG. 5 differs from that described in FIG. 3 in that amplifier 306 may be a solid state pulsed amplifier having a fiber-coupled output that allows the pulse detection laser beam to be delivered via optical fiber.

Figure 6:
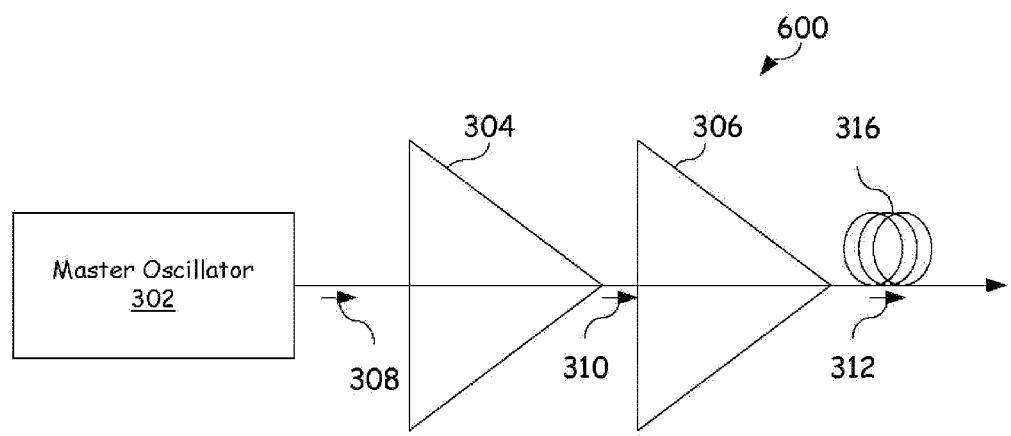
FIG. 6 depicts a pulse detection laser that uses a continuous slab laser pre-amplifier to produce a pulsed detection laser beam in accordance with embodiments of the present invention.

FIG. 6 depicts a pulse detection laser 600 which may be used as detection laser in accordance with embodiments of the present invention. Pulse detection laser 600 includes a single frequency oscillator 302, a continuous pre-amplifier 304, and a pulsed amplifier 306. This embodiment operates similarly to that described with reference to FIG. 3. In this embodiment, pre-amplifier 304 and amplifier 306 of FIG. 6 differ from that described in FIG. 3 in that pre-amplifier 304 may be a diode pumped solid continuous amplifier and amplifier 306 may be a diode pumped solid pulsed amplifier. The components may be optically coupled via free space as shown or optical fiber. The pulsed detection laser beam 312 may be delivered via optical fiber 316.

Figure 7:
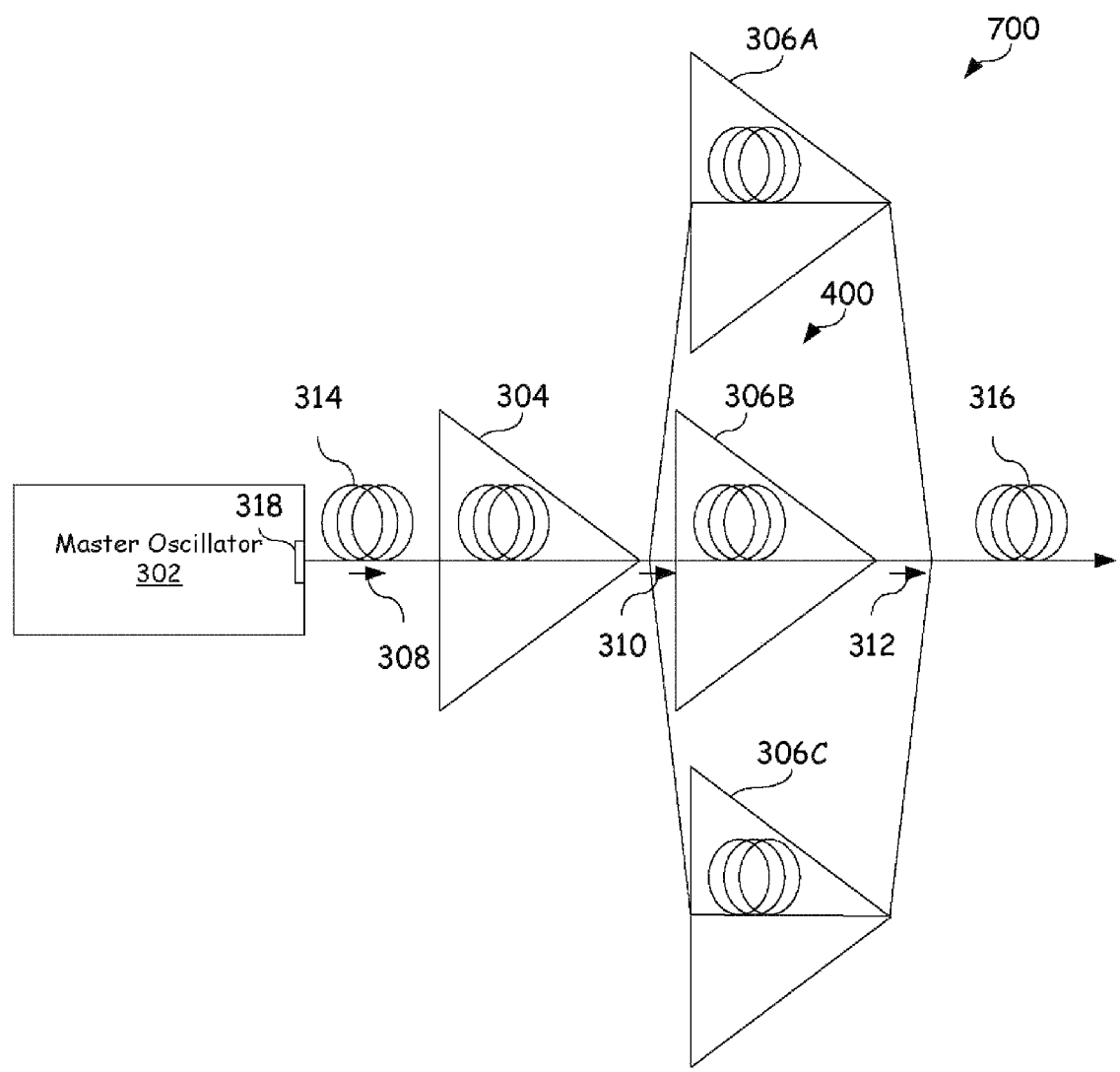
FIG. 7 depicts a pulse detection laser that uses a continuous fiber laser pre-amplifier and parallel diode pumped amplifiers to produce a pulsed detection laser beam that may be used to detect laser ultrasonic displacements in accordance with an embodiment of the present invention.
Figure 8:
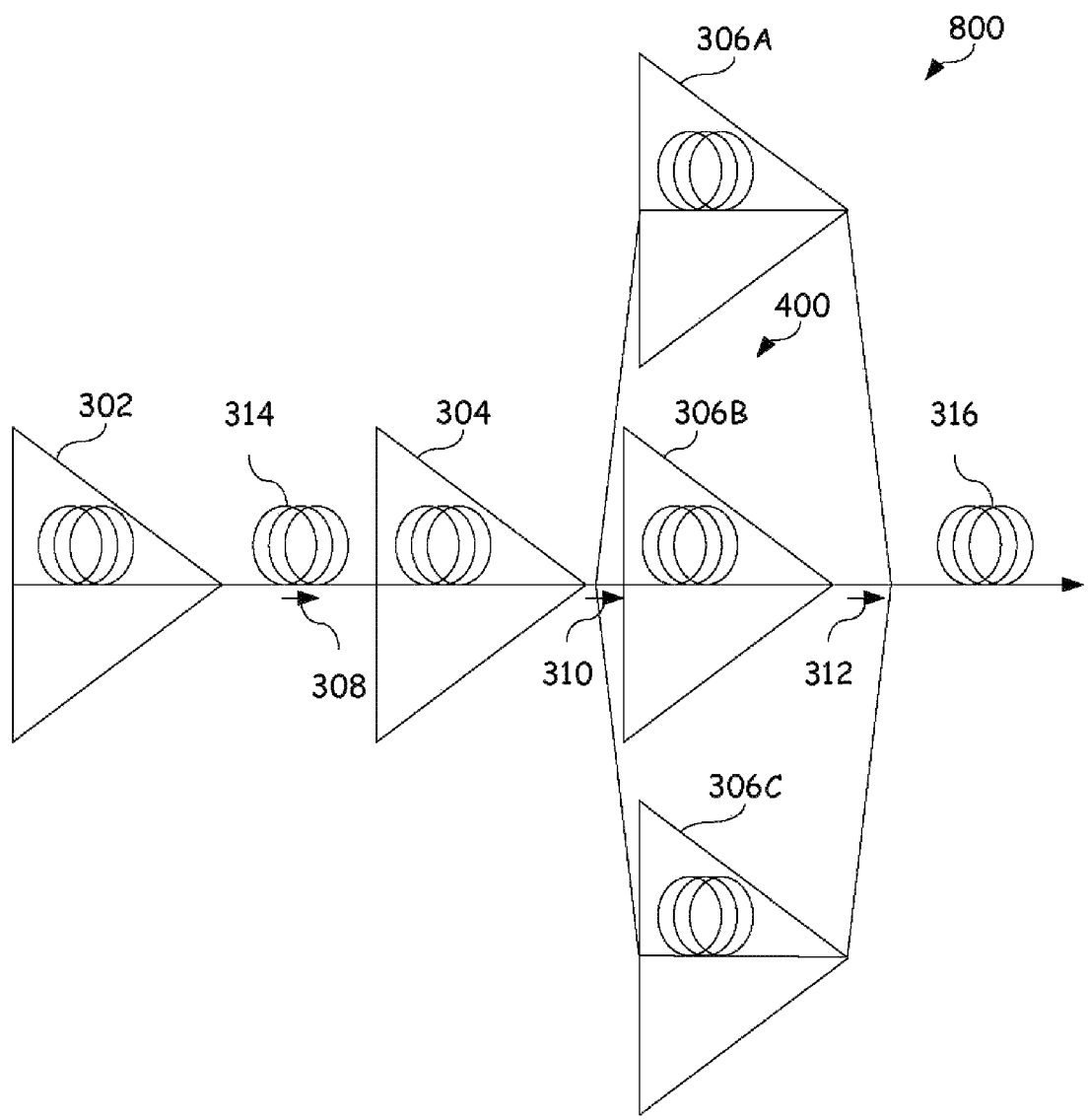
FIG. 8 depicts an all fiber pulse detection laser that uses a continuous fiber laser pre-amplifier and parallel diode pumped amplifiers to produce a pulsed detection laser beam that may be used to detect laser ultrasonic displacements in accordance with an embodiment of the present invention.

The level of power of single-frequency radiation produced by a single amplifier might be limited by a physical phenomenon called stimulated Brillouin scattering (SBS). When SBS occurs, the amplifier acts as a mirror, reflecting the radiation back towards the master oscillator, possibly damaging it and severely limiting the output power. In general, fiber and amplifier fiber are single-mode fibers with typical diameters smaller than 50 microns. The power threshold for which SBS occurs is proportional to the square of the fiber diameter. In order to produce single-frequency radiation at power levels exceeding the power threshold of SBS for the required fiber diameter of the fiber amplifier, several parallel fiber amplifiers can be used, each amplifier producing a power level below its own SBS threshold. The output fibers of all amplifiers are combined by fusion splice or by other technique into a larger multimode fiber that has a SBS threshold above the combined powers of the parallel amplifiers. FIGS. 7 and 8 present this approach as two embodiments of the present invention.

FIG. 7 depicts another embodiment of a pulsed detection laser 700 which may be used as detection laser in accordance with embodiments of the present invention. Pulse detection laser 700 includes a single frequency oscillator 302, a continuous pre-amplifier 304, and a pulsed amplifier 306. This embodiment operates similarly to that described with reference to FIG. 3. In this embodiment, amplifiers 306A 306B and 306C of FIG. 7 differ from amplifier 306 as described in FIG. 3. The output optical fiber 316 is a large core diameter fiber, typically with a diameter larger than 50 microns, and the second stage amplifier has multiple parallel diode-pumped amplifiers 306A, 306, and 306C. The output of these parallel diode pumped amplifiers may be combined within a single optical fiber. Master oscillator 302 produces a seed laser beam 308, which is provided via fiber coupled output 318 to optical fiber 314. In one embodiment of this example, the power output of master oscillator 302 may need to produce a laser beam 308 having a power of about 25 milli-watts. For illustrative purposes, preamplifier 304 may increase the power of this laser beam to approximately 5-10 watts. Then, the three parallel diode pumped fiber amplifiers 306A, 306B, and 306C are each coupled to the output of pre-amplifier 304. Each diode pumped fiber amplifier produces a power below its own SBS threshold. The three parallel diode pumped fiber amplifiers 306A, 306B, and 306C may increase the power of the output laser beam 312 dramatically. As shown in this example, the multimode output may be greater than 1,000 watts when using this configuration of diode pumped fiber amplifiers.

FIG. 8 depicts yet another embodiment of detection laser in accordance with embodiments of the present invention. In this example, master oscillator 302 has been replaced with a diode pumped, single frequency fiber laser as opposed to NPRO.

The fiber laser associated with the master oscillator and the fiber amplifier may be: (1) Ytterbium doped fibers operable to produce radiation at a wavelength of about 1000 nm; or (2) erbium doped or co-doped fibers operable to produce radiation at a wavelength of about 1550 nm. The fiber lasers may use side cladding pumping wherein pumping diodes are coupled to active fiber through pumping fibers. The pumping fibers couple to the active fiber through side cladding or an inner cladding of the active fiber. These pumping diodes may include single emitters, a group of single emitters, diode bars, and/or a group of diode bars.

By using many small continuous wave (CW) diodes to pump the laser fiber, each fiber coupled pump diodes may be relatively small in power (typically only use a few watts). Therefore, the loss of any one or portion of the diodes may have little impact on the total performance of the laser to be generated.

The heat removal problems and thermal distortion of the wave profile of laser beam 312 is greatly reduced by reducing the requirements of the final amplifier. The heat removal from the fiber-coupled diodes may be managed separately from the gain. In addition, these low power diodes typically offer greatly increased mean time between failure (MTBF) ratings that are currently available in slab in diode slab lasers. The thermal management of the fiber laser class amplifier is greatly improved when compared with the use of a traditional bulk crystal gain medium. This is the because the ratio of the fiber surface area (where the heat is removed from the fiber, to the volume where the laser is generated or amplified is many orders of magnitude larger than that of a bulk-surfaced volume ratio associated with a slab amplifier. Thus, the fiber laser may be operated in a single mode with very little wave front distortion. Since the fiber laser can be operated in a CW mode or a modulated-pulse mode, the speed limitation becomes not the laser speed but the ultrasound propagation time within the material to be tested and the scanning capabilities of other components used to scan the detection laser across the components to be tested. This allows effective scan rates to be 10 kHz or higher. This offers a significant improvement when compared to scan rates of existing systems. Additionally, this flexible architecture may enable mobile and portable laser ultrasonic inspection system design suited for harsh industrial environments.

Figure 9:
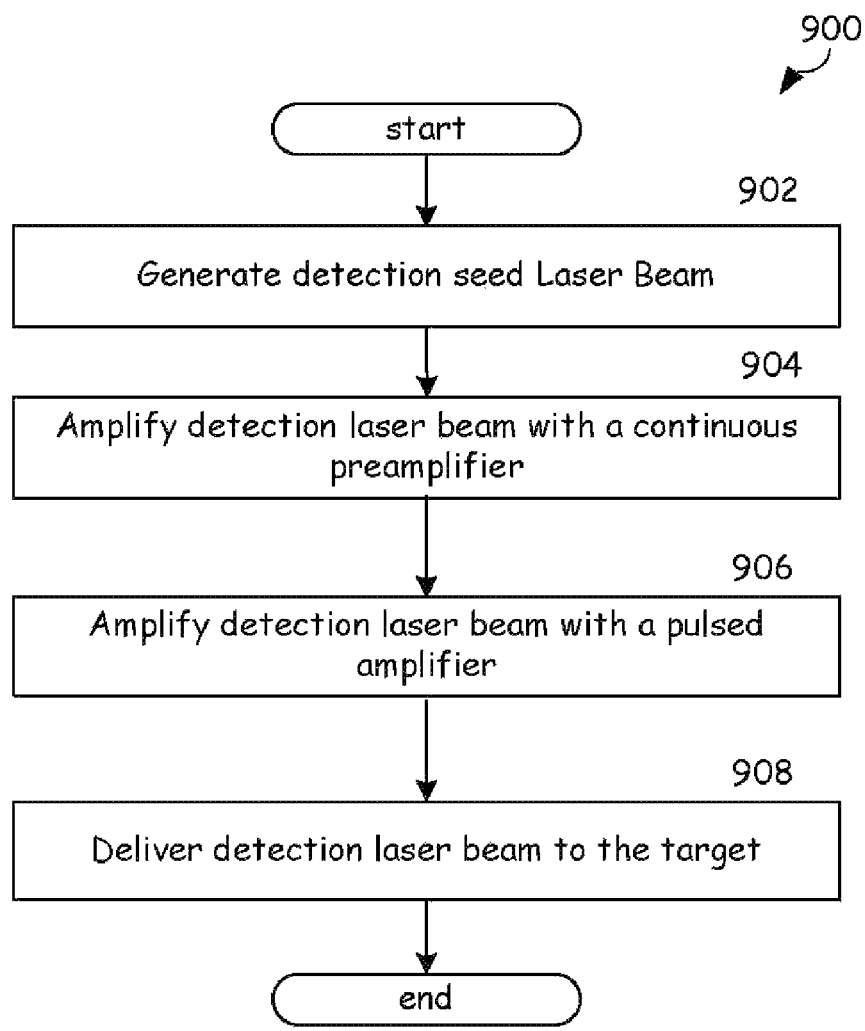
FIG. 9 provides a logic flow diagram in accordance with one or more embodiments for the present invention.

FIG. 9 provides a logic flow diagram in accordance with one or more embodiments for the present invention that depict how the detection laser may be generated within a laser ultrasound inspection system. Operations 900 began with the generation of a seed detection laser in Step 902. This seed detection laser beam may be a low power i.e. on the order of 25 mill-watt laser beam which may be amplified in stages. This seed detection laser beam may be generated using a NPRO or a single pumped single frequency fiber laser or other means known to generate the seed detection laser. The seed laser beam may then be amplified using one or more diode pumped continuous pre-amplifiers in step 904. This results in an intermediate laser beam having an intermediate power level. The intermediate laser beam may then be amplified using one or more diode pumped pulsed amplifies in step 906 to produce the pulsed detection laser. In the embodiment previously depicted various combinations of diode pumped fiber laser amplifiers were employed to increase the power of the detection laser from a 25 milli-watts seed laser to 1,000 or more watts. In step 908 the detection laser beam is delivered to the target.

In operation the present invention allows laser ultrasonic test equipment to be used in a wider range of environments while testing more complex surfaces or surfaces within limited access areas. The embodiments of the present invention may utilize fiber lasers to generate and deliver detection laser beams and possibly generation laser beams to a remote target to be tested. Doing so allows the overall size of a laser ultrasound system to be greatly reduced. For example, instead of a large gantry based system, a much smaller robotic system may be used to deliver generation and detection laser beams to the surface of the target to be tested. This allows the laser ultrasound inspection system offered by embodiments of the present invention to be used to not only inspect individual components but to assess the internal structure of integrated components. Thus, not only can individual parts be inspected by the laser ultrasound system offered by embodiments of the present invention but assembled structures made of individual parts may be inspected. This allows inspections to be made after the integrated structure has been built to see if there are any changes in the internal structure over the life of the structure. Additionally embodiments of the present invention may provide an entirely mobile system that uses fiber lasers to detect ultrasonic displacements at a remote target in the field without the problems often associated with free space delivery of detection of a detection laser beam.

Fiber lasers can produce laser emission at wavelengths similar or identical to the 1064-nm wavelength currently used for industrial laser-ultrasonic inspection by using Ytterbium doped fibers. Ytterbium-doped fibers can therefore replace currently-used diode-pumped or flash-pumped rod or slab detection lasers without the necessity to replace any of the optics and detectors. However, Erbium-doped or Erbium-co doped fibers can produce laser emission at wavelengths around 1550 nm. This wavelength range is commonly qualified as eye-safe. Safety requirements are significantly reduced when using an eye-safe wavelength in comparison to wavelengths around 1000 nm. Those reduced safety requirements could translate in important reduction in capital and operating costs if a laser-ultrasound inspection system were to be used in an open field or in a manufacturing environment.

An additional advantage of using a detection laser operating in a wavelength around 1550 nm is the possibility to leverage the huge quantity of optical technologies like detectors, modulators, optical fibers, etc. developed for telecommunication.

Fiber lasers and fiber amplifiers can be pumped using different approaches. The most popular approach is cladding-pumping where the pumping radiation is inserted in the cladding of the fiber laser or amplifier. Cladding pumping can be done either from the cladding end (end pumping) or the cladding side (side-pumping). Side-pumping eliminates the difficulties of end or coaxial pumping, where off-axis core designs or twisted active and pump fiber designs. In addition, a fused-fiber coupling eliminates the need for focusing optics and alignment, and is more robust than other designs such as end or V-groove pumping By employing individual diodes and a cladding side-pumping technology, the power can be scaled up by the introduction of additional pump diodes with no adverse effect on reliability. The lifetime of the individual diodes is orders of magnitude larger that of diode bars. Additionally, single emitters are independent from each other and when one emitter fails, contrarily to diode bars it does not affect any other emitter. Finally, in case of the failure of a single emitter, the decrease in total output power of the fiber laser or amplifier is very small because of the large number of diode emitters.

In summary, the present invention relate to an improved laser for the optical detection of ultrasound. A pulse detection laser is provided by embodiments of the present invention. The pulse detection laser includes a single frequency oscillator, a continuous pre-amplifier, and a pulsed amplifier. The single frequency oscillator generates a seed laser beam and is optically coupled to the continuous preamplifier. The continuous pre-amplifier amplifies the seed laser to produce an intermediate power laser beam. A pulsed amplifier optically coupled to the continuous pre-amplifier receives the intermediate power laser beam and amplifies the intermediate power laser beam to produce a pulse detection laser beam. One task of this pulse detection laser is to illuminate ultrasonic displacements. Light from the laser is scattered, collected, and analyzed with an interferometer to demodulate the ultrasonic displacements caused by the return echoes of the ultrasound at the surface of the part.

As one of average skill in the art will appreciate, the term "substantially" or "approximately", as may be used herein, provides an industry-accepted tolerance to its corresponding term. Such an industry-accepted tolerance ranges from less than one percent to twenty percent and corresponds to, but is not limited to, component values, integrated circuit process variations, temperature variations, rise and fall times, and/or thermal noise. As one of average skill in the art will further appreciate, the term "operably coupled", as may be used herein, includes direct coupling and indirect coupling via another component, element, circuit, or module where, for indirect coupling, the intervening component, element, circuit, or module does not modify the information of a signal but may adjust its current level, voltage level, and/or power level. As one of average skill in the art will also appreciate, inferred coupling (i.e., where one element is coupled to another element by inference) includes direct and indirect coupling between two elements in the same manner as "operably coupled". As one of average skill in the art will further appreciate, the term "compares favorably", as may be used herein, indicates that a comparison between two or more elements, items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1.

Although the present invention has been described in detail, it should be understood that various changes, substitutions and alterations can be made hereto without departing from the spirit and scope of the invention as defined by the appended claims.

What is claimed is:

1. A method of inspecting an article comprising:
    directing a generation laser beam to produce ultrasonic displacements in a surface of the article;
    generating a continuous seed laser beam with a master oscillator;
    directing the seed laser beam with the master oscillator through free space to a continuous pre-amplifier and amplifying the seed laser beam with the continuous pre-amplifier to produce a continuous intermediate power laser beam;
    directing the intermediate power laser beam through free space without filtering to a pulsed amplifier and amplifying the intermediate power laser beam with the pulsed amplifier to produce a pulsed detection laser beam, and directing the pulsed detection laser beam against the ultrasonic displacements, which scatters the pulsed detection laser beam; and
    optically collecting information about the scattered pulsed detection laser beam and processing the information to determine structural integrity of the article.

2. The method of claim 1, wherein the continuous pre-amplifier comprises continuous wave diode bars.

3. The method of claim 1, wherein the seed laser beam is generated using a diode pumped single frequency fiber laser and wherein the pulsed amplifier comprises diode pumped fiber amplifiers in parallel.

4. The method of claim 1, wherein:
    the intermediate power laser beam is a continuous wave.

5. The method of claim 1, wherein:
    the pulse rate of the detection laser beam ranges from about 50 microseconds to about 100 microseconds.

6. The method of claim 1, wherein the continuous pre-amplifier comprises a continuous slab laser.

7. A laser ultrasound system, comprising:
    a generation laser that directs a pulsed generation laser beam to produce ultrasonic displacements in a surface of an article;
    a single frequency master oscillator for generating a continuous seed laser beam;

a continuous pre-amplifier optically coupled to the single frequency master oscillator via free space for amplifying the seed laser beam to produce a continuous intermediate power laser beam; and a pulsed amplifier optically coupled to the continuous pre-amplifier via free space and without any intervening optical devices, the pulsed amplifier amplifying the intermediate power laser beam to produce a pulsed detection laser beam directed against the ultrasonic displacements in the surface of the article, which causes scattering of the pulsed detection laser beam;

optics that collect information about the scattered pulsed detection laser beam; and a processor that receives the information from the optics to determine structural integrity of the article.

8. The pulsed detection laser of claim 7, wherein the continuous pre-amplifier comprises a slab laser pre-amplifier.

9. The pulsed detection laser of claim 7, wherein the pulsed amplifier comprises
a diode pumped fiber pulsed laser.

10. The pulsed detection laser of claim 7, wherein the pulsed detection laser beam has a pulse period ranges from about 50 microseconds to about 100 microseconds.

11. The pulsed detection laser of claim 7, wherein the pulsed detection laser beam has energy that ranges from about 50 mJ to about 100 mJ.

12. The pulsed detection laser of claim 7, wherein the master oscillator comprises a single frequency oscillator.

13. The pulsed detection laser of claim 7, wherein the intermediate power laser beam has a power of about 5 W to about 10 W and the detection laser has a power of about 500 W to about 1000 W.

14. The method of claim 1, wherein the step of generating the seed laser beam comprises using a master oscillator having components selected from the list consisting of Ytterbium doped fibers operable to produce radiation at a wavelength of about 1000 nm, Erbium doped or co-doped fibers operable to produce radiation at a wavelength of about 1550 nm, and fiber lasers having side cladding pumping wherein pumping diodes are coupled to active fiber through pumping fibers.

15. A composite inspection apparatus for measuring ultrasonic surface displacements on a surface of a remote target comprising:

an ultrasound generation system operable to produce ultrasonic surface displacements in the remote target;

a detection laser operable to illuminate ultrasonic surface displacements on the surface of the remote target with a pulsed detection laser beam, wherein the detection laser comprises:

a single frequency master oscillator operable to generate a seed laser beam;

a continuous pre-amplifier optically coupled via free space to the single frequency master oscillator, the continuous pre-amplifier operable to amplify the seed laser beam to produce a continuous intermediate power laser beam; and a pulsed amplifier optically coupled to the continuous pre-amplifier via free space without any intervening optical devices, the pulsed amplifier operable to amplify the intermediate power laser beam to produce the pulsed detection laser beam;

a scanning assembly operable to create relative motion between an illumination spot of the pulsed detection laser beam and the surface of the remote target;

collection optics for collecting phase modulated light from the pulsed detection laser beam either reflected scattered by the remote target;

an optical processor to process the phase modulated light collected by the collection optics and produce an output signal; and a processor operable to process the output signal to obtain data representative of the ultrasonic surface displacements on the surface of the remote target.

16. The method of claim 1, wherein the ratio of the power between the seed laser beam and the intermediate power laser beam is selected from the list consisting of about 200, 400, 2500, 4000, 5000, and 50,000.

17. The method of claim 1, wherein the ratio of the power between the seed laser beam and the pulsed detection laser beam is selected from the list consisting of about 20,000, 40,000, 250,000, and 500,000.

18. The method of claim 1, wherein the ratio of the power between the intermediate power laser beam and the pulsed detection laser beam is selected from the list consisting of about 10, 50, and 200.

\* \* \* \* \*